United States Patent [19]
Lemontt

[11] Patent Number: 5,658,726
[45] Date of Patent: *Aug. 19, 1997

[54] DETECTING EUKARYOTIC MICROORGANISMS

[75] Inventor: Jeffrey F. Lemontt, West Newton, Mass.

[73] Assignee: Amoco Corporation, Chicago, Ill.

[*] Notice: The portion of the term of this patent subsequent to Jun. 11, 2013, has been disclaimed.

[21] Appl. No.: 860,295

[22] Filed: Mar. 27, 1992

Related U.S. Application Data

[63] Continuation of Ser. No. 173,836, Mar. 28, 1988, abandoned.

[51] Int. Cl.$^6$ .............................. C12Q 1/68; C07H 21/02; C07H 21/04
[52] U.S. Cl. ........................ 435/6; 435/810; 435/921; 435/922; 435/924; 436/501; 536/23.1; 536/24.3; 536/24.32; 935/18; 935/77; 935/78
[58] Field of Search ......................... 435/6, 91, 911, 435/942, 921, 922, 924, 810; 436/501, 815; 536/27, 23.1, 24.3, 24.32; 935/18, 77, 78, 88

[56] References Cited

U.S. PATENT DOCUMENTS 4,358,535  11/1982  Falkow et al. ............................. 435/5

FOREIGN PATENT DOCUMENTS

WO84/02721  7/1984  WIPO .

OTHER PUBLICATIONS

L. de Repentigny, J. Clin. Micro. 21:972, 1985.
Kumar, Infect. Immun. 48:806, 1985.
Magee, J. Bacteriol. 169:1639, 1987.
Zwieb et al. (1981) Nucleic Acids Research, vol. 9, No. 15, pp. 3621–3640.
Olsen et al. (1983) Nucleic Acids Research, vol. 11, No. 22, pp. 8037–8049.
Nelles et al. (1984) Nucleic Acids Research, vol. 12, No. 23, pp. 8749–8768.

*Primary Examiner*—Ardin H. Marschel
*Attorney, Agent, or Firm*—Norval B. Galloway

[57] ABSTRACT

A method for constructing a cDNA probe for use in detecting in a sample, under conditions of predetermined stringency, a target organism belonging to a strain of fungal microorganisms, and not detecting in the sample under such conditions a reference microorganism or any prokaryotic microorganism, includes the steps of determining a nucleotide base sequence in a variable region of small subunit ribosomal RNA from the target organism, the variable region being a region of the small subunit ribosomal RNA that is poorly conserved among eukaryotes and having no corresponding region in prokaryotes; comparing the nucleotide base sequence in the corresponding region of small subunit ribosomal RNA from the reference microorganism, and selecting as a useful probe site a subsequence within the determined sequence; and synthesizing a cDNA complementary to the useful probe site, the cDNA being the probe. Nucleic acid probes are constructed according to the disclosed method. A method for using such a probe for detecting a strain of fungal microorganisms in a sample includes the steps of providing such a probe, deriving RNA from the sample, contacting the probe with the RNA under conditions that allow the probe to hybridize with small subunit rRNA to form hybrid nucleic acid complexes, and detecting the hybrid nucleic acid complexes as an indication of the presence in the sample of the organism. A kit includes such a probe and instructions for its use.

7 Claims, 7 Drawing Sheets

C. albicans cDNA

3' AGGTCGAGGa TTTCGCATAT AATTTCAACA ACGTCAAAtT TTCGAGCATC
AACTTGGAAC CCGAACCGAC CGGCCAGGTA GAAAAACTAC GCATGACCTG
GGTCGGCTCG GAAAGGAAGA CCCATSGTAA ATAMCGCTTG GTCMTGAAAA
TGAAACTTTT TTAATCTCAC AAGTTTCGTC CGGAAACGAG CTTATATAAT
CGTACCTTAT TATCTTATCC TGCAATACCA AGATAAAACA ARCAAAGATC
CTGGTAGCAT TACTAATTAT CCCTGCCAGC CCCCATAGTC ATAAGTCAAC
AGTTCCACTT TAAGAACCTA AATGACTTCT GATT 5' C. albicans

FIG. 2

RNA (642-805)

5' ACCUUGGGCUUGGCUGGCCGGUCCAUCUUUUUGAUGCGUACUGGACCCAG
   || ||||||| || |||||||||| ||||| ||         |||
   ACUUUGGGCCCGGUUGGCCGGUCCGAUUUUUUCGUGUACUGGAUUUCCAA

CCGAGCCUUUCCUUCUGGGUA&CAUUUA............UKGCGAAC
| | ||||||||||||| || | ||| |               ||||||||
CGGGGCCUUUCCUUCUGGCUAACCUUGAGUCCUUGUGGCUCUUGGCGAAC

CAGKACUUUUACUUUGAAAAAAUUAGAGUGUUCAAAGCAGGCCU.UUGCU
||||||||||||||||||||||| |||||||||||||||||||| | |||||
CAGGACUUUUACUUUGAAAAAAUUAGAGUGUUCAAAGCAGGCGUAUUGCU

CGAAUAUAU      3'   C. albicans
|||||||||
CGAAUAUAU           S. cerevisiae

FIG. 2A

C. albicans cDNA probe

3' CCAGGTAGAA AAACTACGCA TGACCTGGGT CGGCTCGGAA AGG   5'

FIG. 2B

DETECTING EUKARYOTIC MICROORGANISMS

This is a continuation of application Ser. No. 07/173,836, filed Mar. 28, 1988, now abandoned.

Part of the work leading to this invention was made with U.S. Government funds. The U.S. Government has certain rights in this invention.

BACKGROUND OF THE INVENTION

This invention relates to detecting eukaryotic microorganisms.

Fungal infection, and particularly invasive systemic candidiasis, is a significant cause of morbidity and mortality in immunocompromised patients. It is important in treatment of invasive candidiasis to obtain a diagnosis early enough to permit application of effective antifungal therapy. Known approaches to premortem diagnosis of candidiasis include isolation of Candida species from blood cultures, serological tests for antibody to Candida, and direct detection of Candida antigens or Candida metabolites in serum.

L. de Repentigny et al. (1985), *J. Clin. Microbiol.*, vol. 21(6), pages 972–79, used enzyme immunoassay and gasliquid chromatography to compare the concentrations of three metabolic markers for candidiasis in serum samples from normal blood donors and high risk patients with and without invasive candidiasis, and concluded that the best approach to diagnosis of invasive candidiasis entails obtaining blood cultures and carrying out serial assays for mannan in serum.

B. V. Kumar et al. (1985), *Infect. Immun.*, vol. 48(1), pages 806–12, showed that human antibodies in blood serum from patients with histoplasmosis reacted most frequently to antigens shared by three disparate fungi, *Histoplasma capsulatum, Candida albicans*, and *Saccharomyces cerevisiae*, while they reacted with low frequency to antigens specific for individual fungal species. Kumar et al. suggested that specific epitopes may be present as part of the shared antigens, and that monoclonal antibodies to, e.g., the mitochondrial fraction of *C. albicans* might be used for specific immunodiagnosis.

B. B. Magee et al. (1987), *J. Bacteriol.*, vol. 169(4), pages 1639–43, found differences in patterns of restriction fragment length polymorphisms ("RFLPs") for the ribosomal DNA ("rDNA") regions from clinical isolates of various species and strains of Candida, and suggested that RFLPs may be clinically useful in biotyping various strains of *C. albicans* or in distinguishing various species.

L. Nelles et al. (1984), *Nucleic Acids Research*, vol. 12(23), pages 8749–8768, proposed an alignment of fourteen small ribosomal subunit RNA ("srRNA") sequences of eukaryotic, archaebacterial, eubacterial, chloroplastic, and plant mitochondrial origin, on the basis of the presence of conserved features in the sequences, such as regions of theoretical secondary structure formation. They identified a number of presumed double-stranded regions ("proposed helices"), and which were present in all the aligned sequences (that is, generally conserved "universal helices"), regions which occurred only in eukaryotic srRNAs (conserved among eukaryotes; "eukaryote-specific helices"), and other regions which were found only in prokaryotic srRNAs (conserved among prokaryotes; "prokaryote-Specific helices"). Nelles et al. proposed a system for numbering the corresponding regions of the aligned sequences. For example, a presumed universal helix, numbered 19 in the Nelles alignment, is at bases having nucleotide numbers 632 through 641 (*A. salina*-specific nucleotide numbering) in each of six eukaryotes in the alignment. They also identified "variable areas," in which the primary as well as the secondary structure appeared to be especially variable among the srRNAs, including, for example, "area V4" (bases 642–870).

Within V4 is a long eukaryotic region (bases 642–805) having low sequence conservation. This region is entirely absent from all the other aligned srRNA sequences from archaebacterial, prokayotic, eukaryotic mitochondrial, and eukaryotic chloroplast sources.

D. E. Kohne, Canadian Pat No. 1 215 904, describes a probe which is complementary to rRNA from any bacteria but is not complementary to human cell rRNA, for detecting the presence of Mollicutes species in human cell culture and other types of bacterial cells; and a method for making the probe. Kohne uses whole *Mollicutes hominis* rRNA as a template for reverse transcriptase synthesis of radioactive cDNA; hybridizes the cDNA to *M. hominis* rRNA to ensure that the cDNA is indeed complementary to this rRNA; then the labeled cDNA is hybridized with an excess of human rRNA, and the fraction not hybridizing to human rRNA is recovered to provide the probe. Kohne also describes using this method, beginning with *Trypanosoma brucei* rRNA, to select a cDNA probe that is complementary to trypanosome rRNA but is not complementary to human rRNA, for detection and quantitation of trypanosomes in human samples by hybridization. Kohne also suggests comparing known nucleotide sequences of rRNA from different organisms to identify "group specific sequences similar to a specific group of organisms", and making as a probe a sequence complementary to such a sequence.

SUMMARY OF THE INVENTION

In general, the invention features, in one aspect, a method for contructing a cDNA probe for use in detecting in a sample under conditions of predetermined stringency a target organism belonging to a strain of fungal microorganisms and not detecting a reference microorganism and not detecting any prokaryotic microorganism. The method includes steps of: determining a nucleotide base sequence in a variable region of small subunit ribosomal RNA from the target organism; comparing the determined nucleotide base region in the variable region from the target organism with the nucleotide base sequence in the corresponding region of small subunit ribosomal RNA from the reference microorganism, and selecting as a useful probe site a subsequence within said determined sequence; and synthesizing a cDNA complementary to the useful probe site, the cDNA being the probe.

The term "eukaryotic microorganisms", as that term is used herein, includes, for example and without limitation, fungi, protozoa, and mammalian cells; the term does not include chlamydia, mycoplasma and the like organisms, such as archaebacteria, intermediate between the conventional eukaryotes and prokaryotes. The term "fungal microorganisms", as that term is used herein, includes, for example and without limitation, molds and yeasts.

The term "variable region", as used herein, is a region of the small subunit ribosomal RNA that is poorly conserved among eukaryotes and that has no corresponding region in prokaryotes. "Corresponding regions", as used herein, are regions of srRNA sequences which, when aligned as in the alignment proposed by Nelles et al., have the same positional relationships with respect to conserved regions, particularly with respect to proposed secondary structures.

In preferred embodiments, the variable region includes at least a part of the region immediately adjacent the 3' end of universal helix 19, that is, it includes at least a part of the region whose bases are assigned numbers 642 through 805 (A. salina-specific numbering) in the Nelles et al. alignment; the target organism is a strain of yeast, particularly a strain of yeast pathologic to humans, more particularly a strain of Candida, and still more particularly a strain of Candida albicans; and the probe has a nucleotide base sequence including at least about 15 consecutive nucleotides selected from the sequence 5' GGAAAGGCTCGGCTGGGTCCAG-TACGCATCAAAAAGATGGACC 3'.

The invention features, in another aspect, an iterative method for contructing a cDNA probe for use in detecting in a sample a target organism belonging to a strain of fungal microorganisms and not detecting any of a plurality of reference microorganisms and probe not detecting any prokaryotic microorganism. The iterative method includes steps of: constructing a cDNA as summarized above and testing it for hybridization with RNA from the reference organisms to determine whether it has the desired specificity; if so, then the cDNA is the probe; but if not, then a refined probe is made by determining the base sequence in the variable region of srRNA from a next one of the reference microorganisms; comparing it with the corresponding base sequences already determined and selecting as a refined useful probe site a subsequence within the determined sequence, and synthesizing a refined cDNA complementary to the refined useful probe site; and testing it for hybridization with RNA from the reference organisms to determine whether it has the desired specificity. If so, then this first refined cDNA is the probe; but if not, the steps are repeated using a next one of the reference microorganisms, until a probe of the desired specificity is obtained.

The method of the invention provides diagnostic probes having as broad a specificity as is desired for a particular use; probes for detecting particular strains or species of fungal microorganisms can be obtained, as well as probes useful for screening groups of strains or species of fungal microorganisms.

In another aspect, the invention features a nucleic acid probe that detects, under conditions of predetermined stringency, the presence in a sample of a first predetermined strain of fungal microorganism and fails to detect under those conditions the presence in the sample both of a second predetermined strain of fungal microorganism and of any prokaryotic organism. The probe includes a nucleic-acid sequence capable of hybridizing, under those conditions, with a subsequence of nucleotide bases including a portion of a nucleotide base sequence of said first predetermined strain, and failing to hybridize, under those conditions, with a second subsequence of nucleotide bases including a corresponding portion of a nucleotide base sequence of the second predetermined strain. The corresponding nucleotide base sequences from the two strains correspond to a variable region that is present in eukaryotic small subunit ribosomal RNA and is not present in prokaryotic small subunit ribosomal RNA.

In another aspect, the invention features a method for detecting in a sample an organism belonging to a strain of fungal microorganisms, the method including providing a probe of the invention, deriving RNA from the sample, contacting the probe with the RNA under conditions that allow the probe to hybridize with small subunit rRNA to form hybrid nucleic acid complexes, and detecting the hybrid nucleic acid complexes as an indication of the presence in the sample of the organism. In another aspect, the invention features a kit, including a probe of the invention, and instructions for its use.

The probes of the invention can be used to detect both viable and non-viable organisms in pure or mixed culture, or directly without culturing in complex samples such as clinical samples or food-related material. The diagnostic test using these probes can be highly sensitive, because the srRNA target molecules are present in high numbers in each cell.

DETAILED DESCRIPTION OF THE PREFERRED EMBODIMENTS

Drawings FIGS. 1A to 1F are a portion of the sequence alignment of srRNAs from a variety of organisms, as proposed by L. Nelles et al. (1984), *Nucleic Acid Research*, vol. 12(23), pages 8749–68.

FIG. 2 is a *Candida albicans* srRNA cDNA sequence, as determined by direct RNA sequencing.

FIG. 2A is an RNA sequence deduced from a portion of the cDNA sequence in FIG. 2, aligned with a corresponding portion shown in Nelles et al. (1984) of the *Saccharomyces cerevisiae* srRNA sequence.

FIG. 2B is the sequence of a synthetic oligomeric cDNA probe complementary to a useful probe site of the RNA sequence shown between arrows in FIG. 2A.

Figure 1A:
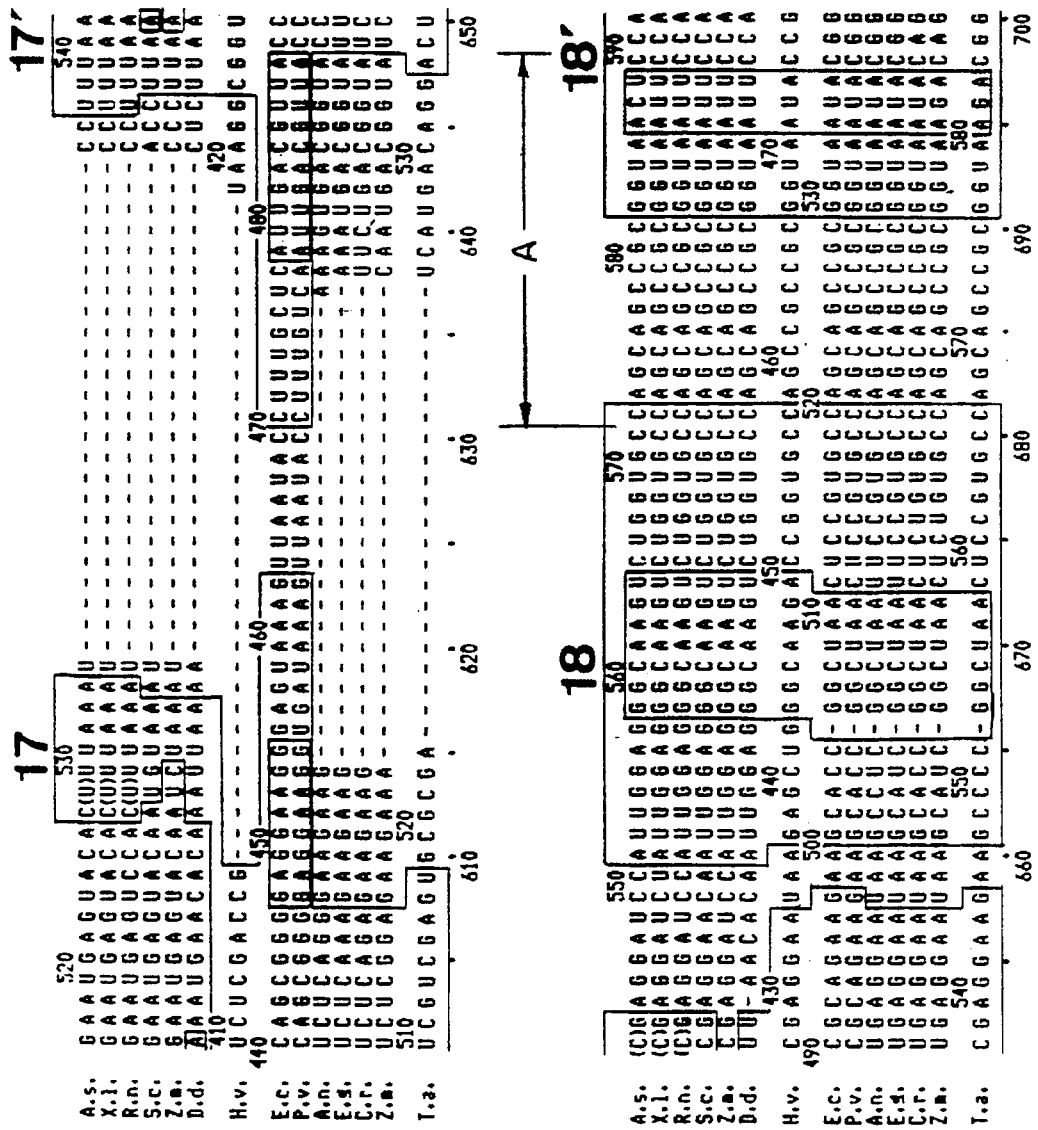
Figure 1B:
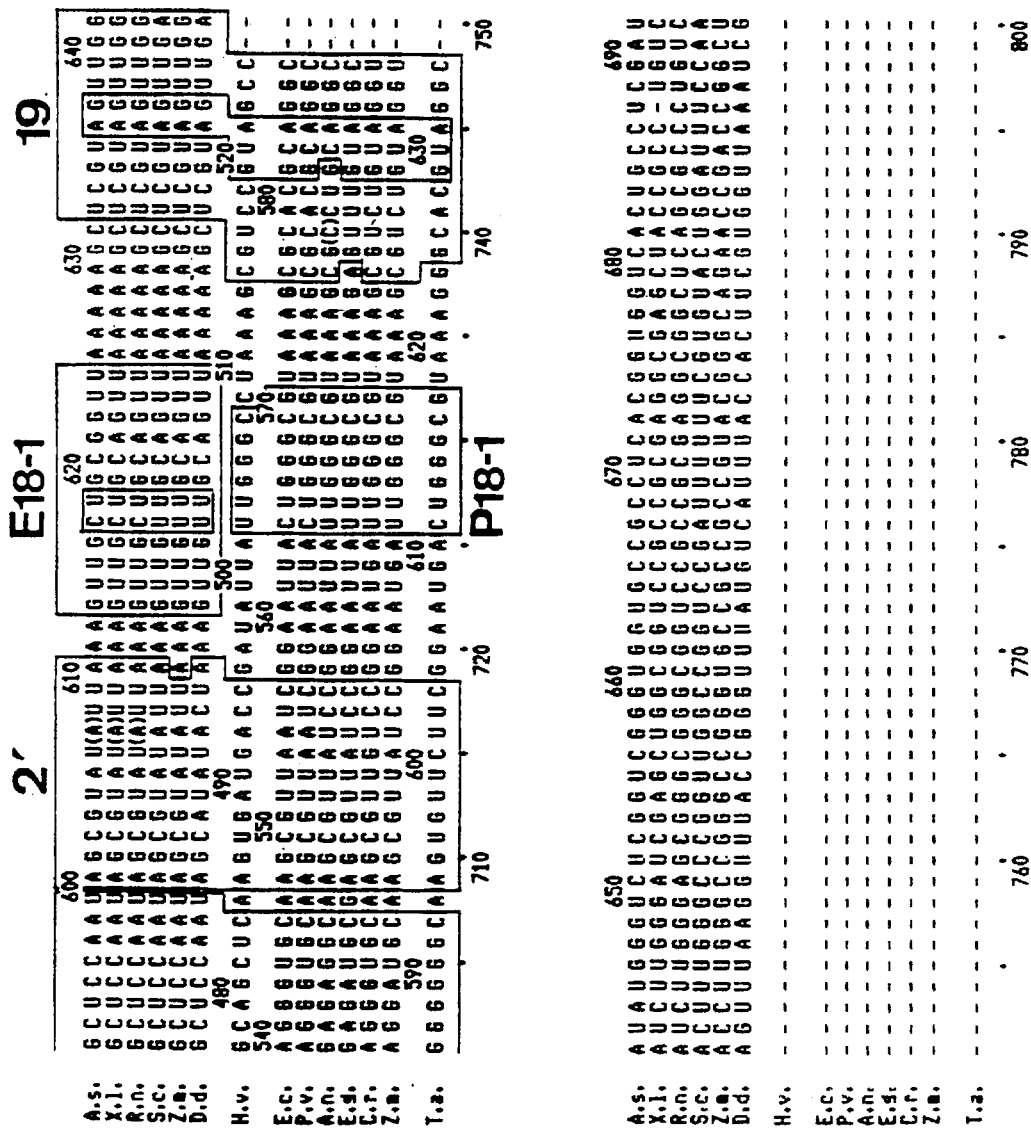
Figure 1C:
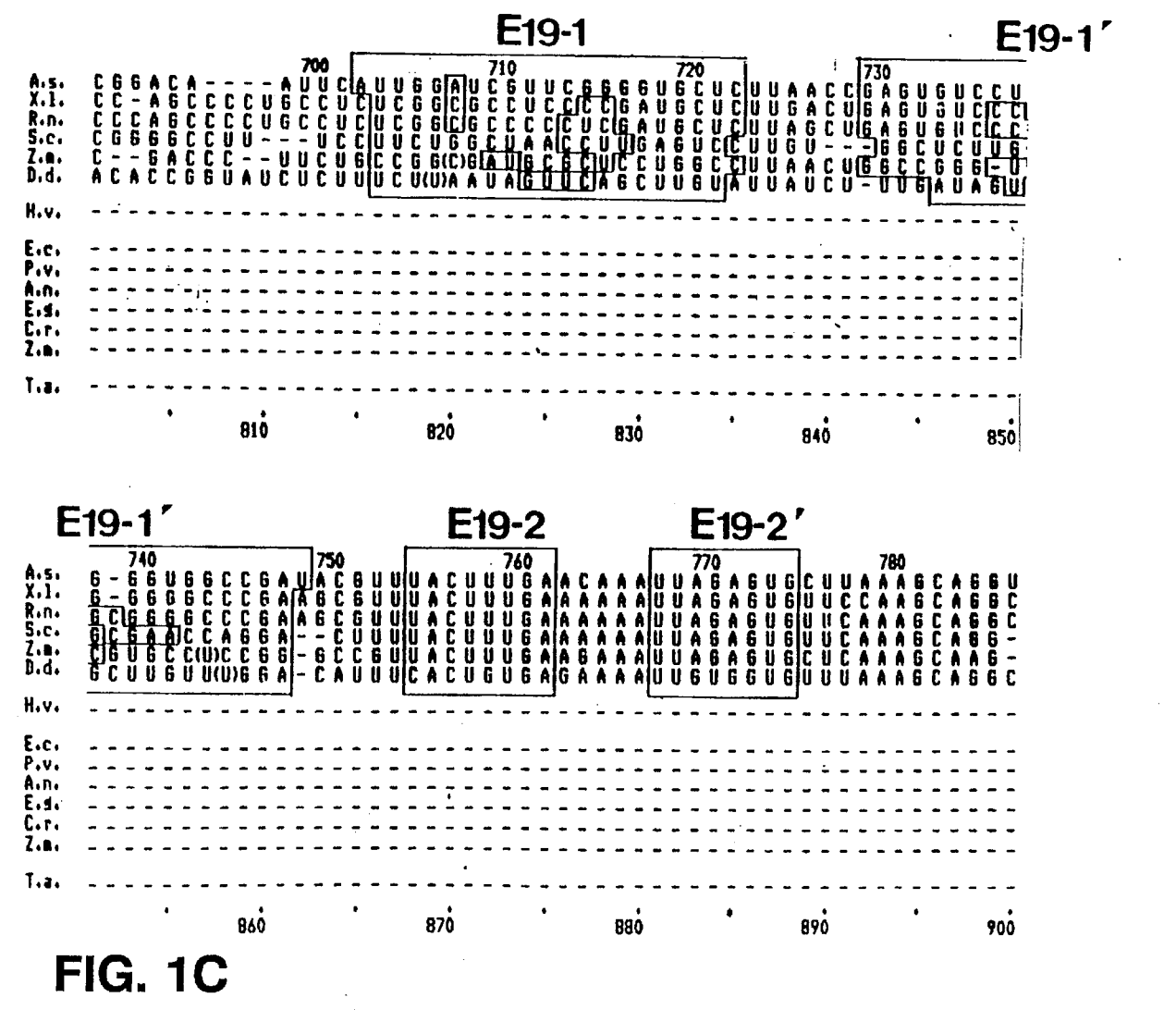
Figure 1D:
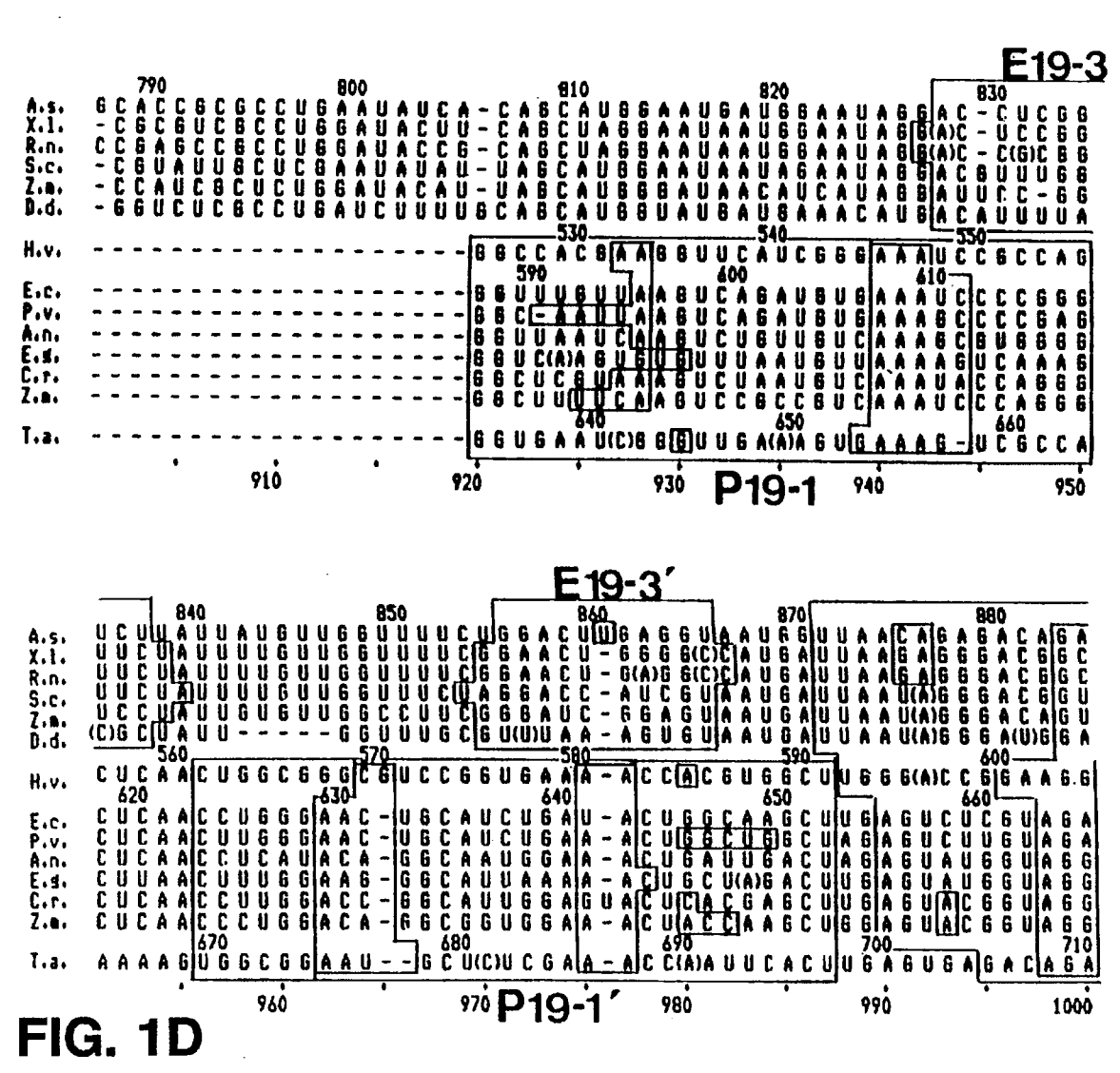

The abbreviations used in the figures are as follows: A, adenine; T, thymine; G, guanine; C, cytosine; U, uracil; M, either cytosine or adenine; R, either guanine or adenine; K, either guanine or thymine; a, adenine (uncertain); t, thymine (uncertain); A.s., *Artemia salina*; X.l., *Xenopus laevis*; R.n., *Rattus norvegicus*; S.c., *Saccharomyces cerevisiae*; Z.m. [upper], *Zea mays*; D.d., *Dictyostelium discoideum*; H.v., *Halobacterium volcanii*; E.c., *Escherichia coli*; P.v., *Proteus vulgaris*; A.n., *Anacystis nidulans*; E.g., *Euglena gracilis* chloroplast; C.r., *Chlamydomonas reinhardtii* chloroplast; Z.m. [lower], *Zea mays* chloroplast; T.a., *Triticum aestivum* mitochondrion. In FIGS. 1A to 1F, smaller numbers are nucleotide numbers specific for *A. salina, H. volcanii, E. coli,* and *T. aestivum* mitochondria srRNA, and are placed above those sequences. The small numbers at the bottom refer to a general numbering system for this alignment. All nucleotide numbers in this application refer only to the *A. salina*-specific numbering appearing at the top. Labeled boxes identify sequences proposed by Nelles et al. as representing regions of common potential secondary structure.

Method of Constructing the Probe

Generally, a probe for detecting a particular eukaryotic organism ("target" organism) is made according to the invention by determining the sequence of nucleotide bases in a region ("variable region") of the srRNA from the target organism that is poorly conserved among eukaryotes and that has no corresponding region in prokaryotes; comparing that determined sequence with the corresponding known sequence from a reference organism whose presence is not to be detected; identifying for use as a probe target sequence ("useful probe site") a subsequence within the determined sequence that is substantially different from the corresponding subsequence in the reference organism; and synthesizing for use as the probe a single-stranded cDNA complementary to the identified probe target sequence. A detailed protocol for carrying out the method follows. One skilled in the art will appreciate that variation in the particulars of the protocol can be made without departing from the invention.

1) Determination of an rRNA sequence of the target organism in a region that is poorly conserved among eukaryotes and that has no corresponding region in prokaryotes ("variable region").

With reference now to FIGS. 1A to 1F, showing a part of the alignment scheme proposed by Nelles et al. (1984), the nucleotide base sequences of the srRNAs from a variety of eukaryotic organisms have a highly variable region, encountered after (i.e., toward the 3' end of the srRNA, and having higher sequence alignment numbers in the Nelles et al. proposed alignment) universal helix 19, for which there is no corresponding region in prokaryotic organisms. The bases in this region are assigned alignment numbers 642 through 805 in the Nelles et al. scheme, and the region is termed herein the "642–805 region".

A modification of the sequencing technique described by Lane et al. (1985) Proc. Natl. Acad. Sci. USA, vol. 82, pages 6955–6959, is employed to determine the srRNA sequence of the particular eukaryotic organism to be detected (the "target organism") in the region between bases numbered 642 and 805 in the Nelles et al. scheme (the "642–805 region"). A 17-base DNA oligomer (5' TTGGCAAAT-GCTTTCGC 3'), which is complementary to a strongly (although not completely) conserved eukaryotic region, that is, bases numbered 947 through 963 in the Nelles et al, scheme, wavy line, FIG. 1E (the "947–963 region"), was used as a specific primer for sequencing the region of interest by reverse transcriptase catalyzed primer extension. When hybridized with a preparation of total cellular RNA from the target organism whose rRNA is to be sequenced, the 17-met anneals to the site at the 947–963 region on the target organism 18S rRNA. The primer fails to anneal to any site on any contaminating prokaryotic (16S) rRNA under comparable stringency conditions. The total cellular RNA fraction may be prepared in any of several ways, but preferably it is prepared by subjecting cell homogenates from the organism to several phenol extractions and several chloroform extractions, followed by ethanol precipitation, NaCl precipitation, and dissolution in water or an aqueous buffer.

Then, cDNA is synthesized as described, for example, in Lane et al., supra, by primer extension catalyzed by AMV reverse transcriptase using mixtures of deoxyribonucleoside triphosphates (dNTP's) and di-deoxyribonucleoside triphosphates (ddNTP's). The cDNA sequence is read directly from gels showing the lengths of primer-extended products in which synthesis has been terminated by incorporation of a ddNTP precursor.

Figure 1E:
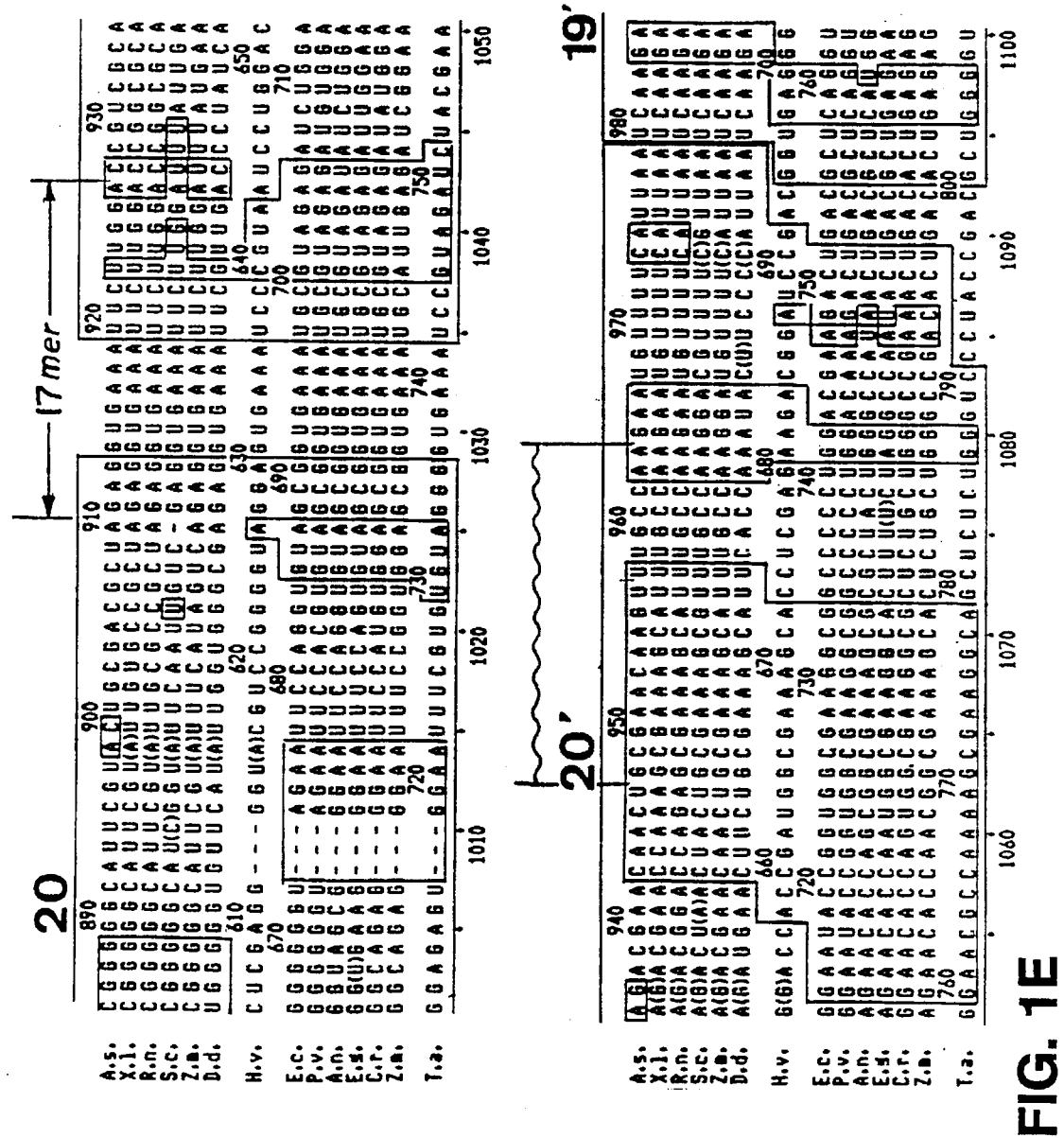
Figure 1F:
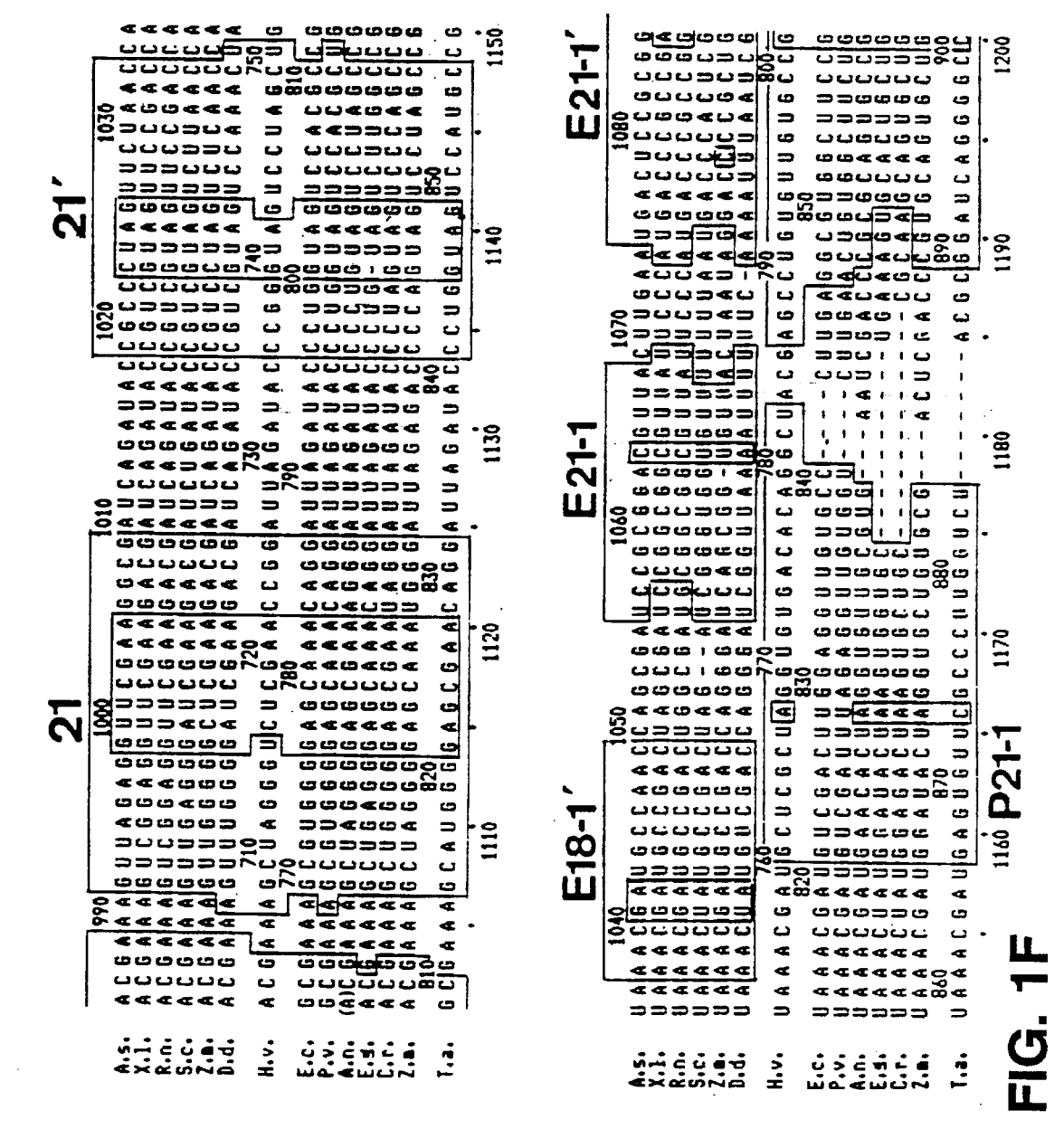

Primers other than the 947–963 region 17-mer also can be used: for example, the region including bases numbered 910 through 926 in the Nelles et al. scheme (the "910–926 region") is conserved among 5 of the 6 eukaryotes shown in FIG. 1E (5' GAGGUGAAAUUCUUGGA 3'), while that of slime mold is the same except for a G at base 922 and a U at base 924. Thus, an equimolar mixture of complementary 17-mers containing two 2-fold redundancies at these positions (5' TC(C/A)A(A/C)GAATTTCACCTC 3') can also be useful as a primer for primer extension synthesis of the 642–805 region.

Then the sequence of bases in the variable region from the organism to be detected, that is, the corresponding 642–805 region, is deduced from the cDNA sequence. It is preferred to deduce the rRNA sequence from the sequenced cDNA rather than from sequenced genomic subclones for several reasons: a) it is much faster since it involves only a small number of steps; b) it is much more efficient in that it minimizes the number of bases sequenced outside the region of interest; c) it is more relevant to development of diagnostic DNA probes in that the cDNA sequence obtained accurately reflects the sequence of the mature 18S rRNA molecules in cells, after all processing of larger precursor molecules has been completed. Although rDNA cistrons tend to be highly amplified in eukaryotic genomes (e.g. in Saccharomyces cerevisiae over 100 direct tandem repeats at a single genomic locus, all of which are transcriptionally active), the rRNA transcription products will be several orders of magnitude more highly amplified. Moreover, with simple disruption procedures used to release rRNA target molecules in a diagnostic test, the relative number of rDNA genes (complexed with chromosomal proteins) released will be very small or nonexistent. Thus, if a certain species were to contain an atypical rDNA gene structure associated with unusual splice sites, for example, then deducing rRNA sequence from sequenced genomic clones might lead to erroneous predictions of the mature 18S rRNA sequence.

2) Comparison of the variable region sequence with the corresponding sequences of one or more organisms not to be detected.

The deduced rRNA sequence of the organism to be detected is now aligned with the corresponding rRNA sequence of the strain or species whose presence is not to be detected by the probe.

For example (this example is described in detail below), in order to design a probe specific detecting the yeast pathogen Candida albicans and not detecting Saccharomyces cerevisiae or any prokaryotes, the 642–805 region sequence from C. albicans organism is first obtained as described above and then aligned with the corresponding sequence from Saccharomyces cerevisiae. The Example below provides a detailed description of how the 642–805 region sequence of Candida albicans can be determined using the general method described above.

3) Analysis of the aligned sequence(s) to determine a subregion containing a useful probe site ("UPS").

The choice of a UPS is made by inspecting the aligned sequences for mismatched bases. Generally the object is to select a UPS such that similarities in the sequence between the organism to be detected and the corresponding portions of the sequence in closely related species (the reference organism) are minimized. Probes designed according to this principle maximize the relative thermal instability, under predetermined conditions of stringency, of hybrids formed by hybridization with the cDNA probe of RNAs from the species not to be detected. One way to accomplish this, for example, is to choose the UPS so that predicted mismatch bases in hybrids are distributed uniformly along the sequence or are clustered near the middle rather than near the ends of the UPS sequence.

4) Synthesis and labelling of a single-stranded oligomeric cDNA probe complementary to the UPS region of the target organism.

The cDNA probe complementary to the target organisms UPS region is preferably synthesized using an automated nucleotide synthesizer. Labelling of the cDNA probe may be performed after synthesis on an automated nucleotide synthesizer by methods well known in the art. For example, the probe can be made to carry a non-radioactive label by using specially modified dNTP precursors during the nucleotide synthesis, as described generally in Rashtchian et al. (1987), Clinical Chemistry, vol. 33(a), pp. 1526–30; and in Applied Biosystems User Bulletin Number 38 (Nov. 3, 1986), pp. 1–5. Alternatively, unphosphorylated 5' ends can be labelled with $^{32}$P following reaction with $^{32}$P-gamma-ATP and polynucleotide kinase enzyme, according to conventional techniques as described generally in, for example, Maniatis et al. (1982), Molecular Cloning, A Laboratory Manual, Cold Spring Harbor, New York.

Finally the probe is proven by testing it for specifically detecting in a sample the presence of the target organism and not detecting the organism whose presence is not to be detected.

Use

The cDNA probes of the invention are used to detect specific eukaryotic microorganisms, particularly Candida species of yeast and other fungi of importance to clinical testing or food testing, according to the following general steps:

1) Disruption of yeast cells or fungal hyphae.

The rRNA from organisms contained in the sample or in cultures derived from the sample is released from the cells by mechanical means, preferably by vigorous vortex mixing of the sample with acid-washed glass beads (about 0.45–0.50 mm diameter) as described generally in C. P. Kurtzman et al., (Review), in: J. F. T. Spencer et al., eds. (1983), Yeast Genetics: Fundamental and Applied Aspects, Springer-Verlag, New York, p. 140.

2) Denaturation of the rRNA.

The cellular homogenate is then treated in well-known fashion with denaturants or with heat (or both) to open up stem-loop or other secondary structures in the target rRNA.

3) Hybridization of sample with cDNA probe.

Then the sample is contacted with the cDNA probe under conditions of stringency in which the probe is known to hybridize with target rRNA. The denatured rRNA can be immobilized on nitrocellulose or nylon membranes and hybridized with the probe in solution. Alternatively, hybridization conditions in which both target and probe are in solution can be used.

4) Removal of non-hybridized probe.

For sample rRNA immobilized on membrane filters, non-hybridized probe can be removed by washing the filters in a solution of salt at a suitable concentration and at a suitable temperature according to well-known methods. For solution hybridizations, any method can be used, preferably a method employing an immobilized anti-DNA:RNA antibody, as described generally in Rashtchian et al., supra, to capture and immobilize RNA-DNA hybrid molecules while non-hybridized probe is removed by subsequent washes.

5) Detection of label in hybridized probe.

Probes labeled with radioactive isotopes can be detected in any of a number of ways, for example by some form of radioisotope counter or by exposure of photographic film. The signal from non-radioactive probes is detected using methods compatible with the type of labelling.

Many variations of the hybridization reaction are possible. For example, steps 1) and 2) can be combined by breaking cells directly in a buffer containing denaturants. For solution hybridizations, cells can be broken in a buffer that also contains the labeled cDNA probe, followed by heat denaturation, then renaturation by cooling. In this case partial hydrolysis of the RNA with mild alkali or ribonuclease can enhance the accessibility of the probe to a site that might otherwise not be fully denatured.

EXAMPLE

The following example demonstrates the manufacture of a Candida-specific rRNA probe according to the invention. Under selected stringency conditions the probe detects the presence of Candida species and does not detect other yeast species or other fungi or prokaryotes. The example is given by way of illustration and is not intended to limit the claims.

The probe was designed and made generally as described above, based on analysis of 18s rRNA sequence data from a strain of *Candida albicans*. The specificity of the probe was assayed against a variety of organisms, including other *Candida albicans* strains, Candida species, and less closely related yeasts and fungi. The organisms used in the specificity assay are listed in Table 1 ("Series A": Candida strains, *Listeria monocytogenes, E. coli*) and Table 2 ("Series B": other yeasts and fungi; human white blood cells).

TABLE 1

| STRAINS (SERIES A) | | |
|---|---|---|
| ORGANISM | STRAIN | OTHER NAMES |
| 1 *Candida albicans* | ATCC 18804* | |
| 2 *Candida albicans* | ATCC 14053 | |
| 3 *Candida albicans* | ATCC 11006 | *Candida stellatoidea* |
| 4 *Candida glabrata* | ATCC 2001* | *Torulopsis glabrata* |
| | | *Cryptococcus glabrata* |
| 5 *Candida tropicalis* | ATCC 750* | |
| 6 *Candida pseudotropical.* | ATCC 4135* | *Candida kefyr* |
| | | *Kluyveromyces fragilis* |
| | | *Kluyveromyces marxianus* |
| 7 *Candida krusei* | ATCC 6258* | *Issatchenkia orientalis* |
| 8 *Candida parapsilosis* | ATCC 22019* | *Monilia parapsilosis* |
| 9 *Candida quilliermondii* | ATCC 6260* | *Pichia quilliermondii* |
| 10 *Candida lusitaniae* | ATCC 42720 | *Clavispora lusitaniae* |
| 11 *E. coli* | YMC | |
| 12 *Listeria monocytogenes* | SLCC 6933, SLCC 6835 | |

*Type culture

TABLE 2

| STRAINS (SERIES B) | | |
|---|---|---|
| ORGANISM | STRAIN | OTHER NAMES |
| 1 *Saccharomyces cerevisiae* | X2180-1A | |
| 2 *Schizosaccharomyces pombe* | ade6 | |
| 3 *Schwanniomyces castellii* | ATCC 26076 | |
| 4 *Yarrowia lipolytica* | ATCC 32338 | *Candida lipolytica* |
| | | *Saccharomycopsis lipolytica* |
| 5 *Saccharomyces uvarum* | comm. beer | *Saccharomyces carlsbergensis* |
| 6 *Trichosporon capitatum* | ATCC 10663 | *Geotrichum capitatum* |
| | | *Blastoschizomyces capitatus* |
| 7 *Trichosporon beigelii* | ATCC 28592* | *Geotrichoides cutaneus* |
| | | *Trichosporon cutaneum* |
| 8 *Trichophyton mentagrophytes* | ATCC 28185 | *Arthroderma benhamiae* |
| 9 *Trichophyton rubrum* | ATCC 28188 | |
| 10 *Alternaria alternata* | ATCC 13963 | tomato black mold |
| 11 Human White Blood Cells | | |

*Type culture

1) Preparation of *Candida albicans* total RNA.

*Candida albicans* (ATCC strain 18804) yeast cells exponentially growing at 30° C. in 50 ml of liquid YEPD medium (1% yeast extract, 2% peptone, 2% dextrose) were distilled water-washed by low-speed centrifugation, suspended in 3 ml of an RNA extraction buffer (0.1M LiCl, 0.1M EDTA, 0.1M Tris-HCl, pH 7.4), and placed on ice. Two grams of acid-washed and distilled water-rinsed glass beads (0.45–0.50 mm diameter) were added and the mixture repeatedly shaken at the highest speed on a vortex mixer for 10 sec, and then placed in an ice bath for 10 sec, until a total time of 2 min had elapsed. Then, 0.05 ml of 10% sodium dodecylsulfate (SDS) and 1 ml of phenol (equilibrated with 10 mM Tris-HCl, 1 mM EDTA, pH 8.0) were added and the mixture agitated briefly. Following low-speed centrifugation to separate the phases, the top aqueous phase was removed and twice again extracted with phenol, then twice extracted with chloroform-isoamyl alcohol (24:1) and then adjusted to 0.3M sodium acetate. Total nucleic acids (RNA and small plasmid DNA) were precipitated with 2 volumes of 100% ethanol. The precipitates were washed once with 70% ethanol and once with 100% ethanol, dried under vacuum, dissolved in sterile distilled water, and stored at −20° C. High molecular weight RNA was further separated from DNA and from low molecular weight RNA by precipitation with 2M NaCl.

The resulting solution was diluted in distilled water and the UV absorption measured at 260 nm. Concentration of nucleic acid was determined on the basis of $A_{260}=1.0$ (1-cm path length) for 50 micrograms per ml. Subsequent analysis by agarose gel electrophoresis revealed that greater than 99% of the nucleic acid stained by ethidium bromide is composed of a mixture of 18S and 25S subunit rRNAs.

2) Obtaining a *Candida albicans* srRNA cDNA sequence.

A cDNA sequence was obtained by generally following the primer-extension method described in Lane et al. (1985) *Proc. Natl. Acad. Sci. USA*. vol. 82, pages 6955–6959, using as a template the *Candida albicans* total RNA preparation described above and using as a primer the synthetic oligomeric DNA sequence 5' TTGGCAAATGCTTTCGC 3' (FIG. 1E, wavy line). The cDNA sequence obtained is shown in FIG. 2.

3) Identification of a possible useful probe site ("UPS") and synthesis of a cDNA probe.

The deduced RNA sequence of the *C. albicans* srRNA in the 642–805 region then was compared with the corresponding region, shown in Nelles et al. (1984), from *Saccharomyces cerevisiae*, by aligning the sequences as shown in FIG. 2A.

One possible UPS, shown between arrows in FIG. 2A, was chosen by inspection of the aligned sequences. A 43-nucleotide oligomeric DNA complementary to this UPS (shown in FIG. 2B) was synthesized on an automated nucleotide synthesizer. The 43-mer was gel-purified and labeled at the 5' end with $^{32}$P, following reaction with $^{32}$P-gamma-ATP and T4 polynucleotide kinase enzyme. The end-labeled 43-mer *C. albicans* rRNA probe was gel-purified and assayed for specificity by hybridization reactions with various total RNA preparations from other eukaryotic organisms.

4) Assay for probe specificity.

The specificity of the 43-mer probe was tested empirically by first preparing total RNA from a collection of organisms (Tables 1 and 2) using methods the same as or similar to that described above for *C. albicans*. RNAs were denatured by dilution into a solution containing final concentrations of 7.5% formaldehyde and 10× SSC (1× SSC is 0.15M sodium chloride, 0.015M sodium citrate, pH 7.0), followed by heating to 50° C. for 15 min., then quick cooling by immersion in an ice bath. Equal amounts (approx. 1 microgram) of denatured RNA from each strain were immobilized on 2 different nylon membrane filters. One filter was hybridized with the labeled 43-met test probe, while the other was hybridized with a similarly end-labeled oligomeric DNA probe. This latter probe is an equimolar mixture of 4 different 18-mers that are complementary to the 572–589 region (region A, FIG. 1A): 5' G(A/T)ATTACCGCGGC(G/T)GCTG 3'. This latter probe is used here as a control for the amount of denatured 18s rRNA immobilized on the filters because this region is very strongly conserved among small subunit rRNAs of all organisms (Lane et al. (1985) have described these 18-mers as "universal primers" for use in the cDNA primer-extension sequencing technique).

Filters were hybridized overnight (greater than 16 hours) under low-stringency conditions at room temperature in a simplified cocktail containing 1 mg/ml salmon sperm DNA (sonicated and heat-denatured), 0.5% SDS, 6× SSC, then subjected to low-stringency (6× SSC, 37° C.) or high-stringency (0.1× SSC, 65° C.) washes. The assay for hybridization was by exposure to X-ray film.

The 43-mer probe detected strains of only 3 other Candida species, besides the *Candida albicans* controls: *Candida tropicalis*, *Candida parapsilosis*, and *Candida guilliermondii* (weak positive). Following the initial low-stringency wash, all other strains in this collection (Tables 1 and 2) were essentially negative or only very slightly positive with the 43-met probe. Following a high-stringency wash, the same pattern of hybridization obtained; the strains showing slight positives after low stringency show negative under high stringency. Results with the control 18-mars showed that all samples hybridized approximately equally well, showing that approximately equal amounts of hybridizable RNA were present on the filter.

Regarding the detection of Candida species and other unrelated yeasts and fungi comprising our test panel, the desirable negative test-probe results indicate a lack of hybridization rather than a lack of RNA, because in such cases the results of the positive control probe was positive. This indicates that hybridization took place and hence that hybridizable RNA was present. The sample derived from human white blood cells contains mostly DNA (only a small fraction is 18S and 28S rRNA). This is consistent with the observed results wherein the test probe did not hybridize but the positive control probe did, albeit weakly.

5) Assay for greater specificity under higher stringency.

Candida strains A1–A9 (Series A; Table 1) were examined by hybridization analysis with the 43-met test probe under higher stringency conditions than those employed as described in section 4, above. For each strain, both a purified total RNA sample and a cell suspension sample were tested. The RNA sample was prepared as described above. Cells were suspended in distilled water and adjusted to a uniform turbidity corresponding to absorbance at 600 nm of 0.5. Equal aliquots of 0.3 ml of the cell suspension were adjusted to contain final concentrations of 10× SSC and 7.5% formaldehyde in a final volume of 1.0 ml, in 13 mm×100 mm glass culture tubes. Two grams of glass beads were added and the tubes containing the mixture were placed in an ice bath, shaken at high speed on a vortex mixer for 30 seconds, incubated at 50° C. for 15 min, and quickly cooled in an ice bath. 0.2 ml of the resulting homogenate (free of glass beads, which had quickly settled out) was immobilized on a nylon membrane filter and hybridized for 90 minutes with the labeled 43-mer *C. albicans* rRNA probe in 6× SSC at 65° C. The filters were then washed in 6× SSC at 65° C. and assayed by exposure to X-ray film. The filters were also subsequently washed in 0.1× SSC at 65° C. and assayed by exposure to X-ray film.

Under these conditions, *Candida tropicalis* was detected by the *C. albicans* rRNA-derived probe following the 6× SSC wash but not following the 0.1× SSC wash (approximately 99% of the radioactivity was lost in the high-stringency wash). Following the 0.1× SSC wash, *Candida parapsilosis* showed strong positive, while *Candida guilliermondii* showed weak positive. Moreover, positive signals were obtained from samples derived from whole yeast cells only in cases where the purified RNA samples are also strongly positive. Candida strains (Table 1) not detected with the 43-mer probe are negative for both purified RNA and whole-cell samples.

This *C. albicans*-derived srRNA 43-mer probe is thus demonstrably useful in a diagnostic assay for the presence of Candida yeast cells. The probe failed to detect non-Candida yeasts and other unrelated fungi or prokaryotic organisms (section 4 above), while at the same time detecting all tested Candida species known as actual or potential human pathogens, with the exceptions of *Candida glabrata*, *Candida krusei*, *Candida kefyr*, and *Candida lusitaniae*. In addition, it detected *C. parapsilosis* and *C. guilliermondii*. Determination and alignment of sequences for *Candida parapsilosis* and *Candida guilliermondii*, using the general method described above, can provide both more specific probes and more general probes, including Candida-specific, yeast-specific, and fungi-specific probes.

Total RNA samples (5 micrograms each) from strains A1–A7 (Candida species), A11 (*E. coli*), B1 (*Saccharomyces cerevisiae*), B6 (*Trichosporon capitatum*), and B9 (*Trichophyton rubrum*) were denatured with formaldehyde and heat and then analyzed by electrophoresis through a 1.2% agarose gel containing formaldehyde. Ethidium bromide staining confirmed that all samples contained approximately equal abundances of major rRNA subunits (i.e. approximately uniform staining of 16S, 18S, 23S, and 25S bands). Following Northern blot transfer and immobilization on a nitrocellulose membrane, the filter was probed with the *C. albicans*-derived 43-mer under the same hybridization and wash conditions as described above. Single bands of strongly positive hybridization were observed only in *Candida albicans* strains A1–A3 at a position corresponding to the migration of the ethidium bromide-stained 18S rRNA subunit. The 25S subunits exhibited no hybridization whatsoever, nor was there any hybridization detectable anywhere else throughout the fractionated total RNA samples. The 18S subunit from strain A5 (*Candida tropicalis*) exhibited a weaker hybridization signal than that from the other three strains. Fractionated total RNAs from all the other samples failed to exhibit any hybridization with the 43-mer probe. This example shows that positive hybridization exhibited by these total RNA samples was due to presence of 18S rRNA sequences homologous with and complementary to the *C. albicans*-derived 43-mer srRNA cDNA probe.

6) Further refinement of probe specificity.

The method of the invention can be used to make a more narrowly specific *Candida albicans* probe, that is, a probe that detects *C. albicans* and does not detect *C. parapsilosis* or *C. guilliermondii*, or to make a probe that detects a selected group of species, such as, for example, selected known actual or potential human pathogens, including *C. glabrata*, *C. krusei*, *C. kefyr*, and *C. lusitaniae*.

Making a more narrowly specific probe requires elimination of "false positives". In the above example, detection of *C. parapsilosis* and *C. guilliermondii* can be eliminated by determining the variable region base sequence of the srRNA from one of the species, preferably *C. parapsilosis*, the more strongly positive one, aligning the base sequence with known variable region sequences, identifying a potential UPS by inspection of the alignments, and then synthesizing and testing a cDNA to the UPS. The potential UPS can be chosen as one which would hybridize to *C. albicans* but not to *C. parapsilosis* or to other species whose variable region sequences are known and included in the alignment. False positives, if any, detected in the test of this refined probe can be eliminated by iteration of the above steps. Only variable region sequences of particular false positives need be determined, and elimination of one such false positive can result in elimination as well of one or more others, so that not all sequences need be determined. A tremendous savings of steps and resources can thereby be realized.

Making a probe that detects a selected broader group of strains or species amounts to eliminating "false negatives". In the above example, detection of *C. glabrata*, *C. krusei*, *C. kefyr*, and *C. lusitaniae* can be obtained by determining the variable region base sequence of one of these species, for example, *C. glabrata*, aligning the base sequence with known variable region sequences, identifying a known UPS by inspection of the alignments, and then synthesizing and testing a cDNA to the UPS. The potential UPS can be chosen as one complementary to a DNA probe that would hybridize with both *C. albicans* and *C. glabrata*, but not with other species whose variable region sequences are known and included in the alignment. False negatives, if any, detected in the test of this refined probe can be eliminated by iteration of the above steps. As is the case with refinement to eliminate false positives, elimination of one false negative can result in elimination as well of one or more others, so that here, too, not all sequences need be determined.

In this manner, a probe having a desired breadth of specificity for a particular species or strain or group of species or strains of fungal microorganisms can be made for any clinical or food-related setting.

Other Embodiments

Other embodiments are within the following claims. For example, probes can be made and used according to the invention for fungal microorganisms other than *Candida albicans*. Of particular interest are other fungal pathogens of humans, including, for example, yeast-like pathogens such as species of Geotrichum; non-yeast dermatophytes such as species of Trichophyton, Microsporum, and Epidermophyton; and systemic and non-systemic yeast pathogens such as species of Cryptococcus, Coccidioides, Histoplasma, Blastomyces, and other species of Candida.

I claim:

1. A method of detecting a Candida organism in a biological sample, said method comprising the steps of:
   (a) isolating Candida RNA, if present, from said biological sample;
   (b) contacting said Candida RNA, if any, with a nucleic acid probe which specifically hybridizes to srRNA from said Candida organism but not to nucleic acid from non-Candida organisms, said probe consisting of a nucleotide sequence of 15 or more consecutive nucleotides within region 642–805 of the small ribosomal RNA of said Candida organism, or a sequence of 15 or more consecutive nucleotides complementary to a segment of said region;
   (c) imposing hybridization conditions on said probe and said Candida RNA which permit hybrid formation between said probe and said RNA and do not allow stable hybrid formation between said probe and RNA of non-Candida organisms; and
   (d) detecting said hybrid as an indication of the presence in said sample of said Candida organism.

2. The method of claim 1, wherein said Candida organism is *C. albicans, C. tropicalis, C. parasilosis,* or *C. guilliermondii*.

3. The method of claim 1, wherein said nucleic acid probe consists of a nucleotide sequence identical or fully complementary to a nucleotide sequence of at least 15 and up to 43 consecutive nucleotides in length, which sequence is within the sequence:

5' GGAAAGGCTCGGCTGGGTCCAGTACG-CATCAAAAAGATGGACC 3'.

4. A nucleic acid probe which specifically hybridizes to rRNA from a Candida organism but not to nucleic acid from a non-Candida organism, said probe containing a nucleotide sequence of 15 or more consecutive nucleotides within region 642–805 of the small ribosomal RNA of said Candida organism, or a sequence of 15 or more consecutive nucleotides a segment of said region.

5. The nucleic acid probe of claim 4, said probe consisting of a nucleotide sequence identical or fully complementary to a nucleotide sequence of at least 15 and up to 43 consecutive nucleotides in length, which sequence is within the sequence:

5' GGAAAGGCTCGGCTGGGTCCAGTACG-CATCAAAAAGATGGACC 3'.

6. A kit comprising the isolated nucleic acid probe of claim 4.

7. The nucleic acid probe of either of claims 4 or 5, said probe further comprising a label.

* * * * *